United States Patent [19]

Sebag et al.

[11] Patent Number: 5,275,755
[45] Date of Patent: Jan. 4, 1994

[54] WASHING COMPOSITIONS BASED ON SILICONE AND ON FATTY ALCOHOLS CONTAINING ETHER AND/OR THIOETHER OR SULPHOXIDE GROUPS

[75] Inventors: Henri Sebag, Paris; Claude Dubief, Le Chesnay; Bernard Beauquey, Clichy, all of France

[73] Assignee: L'Oreal, Paris, France

[21] Appl. No.: 702,094

[22] Filed: May 20, 1991

[30] Foreign Application Priority Data

May 18, 1990 [FR] France .................................. 90 06279

[51] Int. Cl.$^5$ ................................................ C11D 1/90
[52] U.S. Cl. .......................... 252/174.15; 252/174.21; 252/DIG. 13; 252/DIG. 4
[58] Field of Search ....................... 252/174.15, 174.21, 252/DIG. 4, DIG. 13; 424/70

[56] References Cited

U.S. PATENT DOCUMENTS 4,741,855 5/1988 Grote et al. ........................ 252/142

FOREIGN PATENT DOCUMENTS 0373661 6/1990 European Pat. Off. .
2851832 6/1980 Fed. Rep. of Germany .
2060665 5/1981 United Kingdom .

*Primary Examiner*—Olik Chaudhuri
*Assistant Examiner*—C. Everhart
*Attorney, Agent, or Firm*—Jacobson, Price, Holman & Stern

[57] ABSTRACT

Composition for washing keratinous materials, especially the hair and the skin, characterised in that it comprises, in an aqueous medium, at least one silicone, at least one surfactant possessing detergent properties and at least one alcohol having 27 to 44 carbon atoms and containing one or two ether and/or thioether or sulphoxide group(s), corresponding to the formula (I):

$$R_1-X+C_2H_3(OH)+CH_2-Y-R_2 \qquad (I)$$

in which
 $R_1$ and $R_2$, which may be identical or different, denote linear $C_{12}$ to $C_{20}$ alkyl groups;
 X denotes an oxygen atom, a sulphur atom or a sulphoxide group;
 Y denotes an oxygen atom, a sulphur atom, a sulphoxide group or a methylene group;
 in the case where Y denotes a methylene group, the sum of the numbers of carbon atoms in $R_1$ and $R_2$ varies from 24 to 40, and preferably from 26 to 36, inclusive, and when Y does not denote a methylene group, the sum of carbon atoms in $R_1$ and $R_2$ varies from 24 to 40 inclusive, and preferably from 28 to 36 inclusive; when X or Y denotes sulphoxide, Y or X does not denote sulphur.

34 Claims, No Drawings

WASHING COMPOSITIONS BASED ON SILICONE AND ON FATTY ALCOHOLS CONTAINING ETHER AND/OR THIOETHER OR SULPHOXIDE GROUPS

The present invention relates to compositions for washing and conditioning keratinous materials, especially the hair and/or the skin, based on silicone, on surfactants and on a fatty alcohol containing an ether and/or thioether or sulphoxide group, as well as to the washing processes employing these compositions.

Compositions for washing keratinous materials, in particular shampoos, are well known in the prior art. It has already been proposed in the past to use silicones in such compositions in order to impart to the materials being treated, in particular the hair, good conditioning properties such as softness, sheen and ease of disentangling.

In view of the insoluble nature of the silicones which are usable in washing and conditioning compositions, it is endeavoured to maintain the silicones evenly dispersed in the medium without, however, causing a drop in the viscosity and the detergent and foaming properties of the compositions. The silicones must also be carried to the keratinous materials being treated for the purpose of imparting to them, according to the application, properties of softness, sheen and disentangling.

The Applicant discovered, and this forms the subject of the invention, that, by using at least one alcohol having 27 to 44 carbon atoms and containing one or two ether and/or thioether or sulphoxide group(s) in washing compositions based on insoluble silicones and on surfactants, it was possible to prepare compositions displaying very good homogeneity and improved stability, as well as a satisfactory viscosity for application to keratinous materials.

The compositions thus prepared possess good detergent and foaming properties, and impart great softness to keratinous materials, in particular the hair and/or skin.

These compositions, when applied to the hair, possess, in addition to their washing properties, properties of conditioning the hair, that is to say the treated hair is shiny, disentangles easily and is soft to the touch.

The subject of the invention is hence new washing compositions based on silicone, on surfactants and on ether- and/or thioether- or sulphoxide-containing alcohols.

Another subject of the invention consists of the washing process employing such compositions.

Other subjects of the invention will become apparent on reading the description and the examples which follow.

The compositions for washing keratinous materials, especially the hair and the skin, according to the invention, comprise, in an aqueous medium, at least one silicone, one surfactant possessing detergent properties and at least one alcohol having 27 to 44 carbon atoms and containing one or two ether and/or thioether or sulphoxide group(s), corresponding to the formula (I)

$$R_1-X+C_2H_3(OH)+CH_2-Y-R_2 \quad (I)$$

in which
$R_1$ and $R_2$ denote, independently of one another, linear $C_{12}$ to $C_{20}$ alkyl groups;

X denotes an oxygen atom, a sulphur atom or a sulphoxide group;

Y denotes an oxygen or sulphur atom or a sulphoxide or methylene group;

in the case where Y denotes a methylene group, the sum of the number of carbon atoms present in the groups $R_1$ and $R_2$ has a value varying from 24 to 40, and preferably from 26 to 36, inclusive;

when Y does not denote a methylene group, the sum of the carbon atoms in $R_1$ and $R_2$ has a value varying from 24 to 40 inclusive, and preferably from 28 to 36 inclusive;

when X or Y denotes sulphoxide, Y or X does not denote sulphur.

The compounds used preferentially according to the invention are those in which X denotes oxygen, Y denotes methylene and $R_1$ and $R_2$ denote radicals having 12 to 18 carbon atoms.

The compounds of formula (I) are obtained by reacting a compound containing active hydrogen, of formula (II):

$$R_1XH$$

with a compound containing a terminal oxirane group and corresponding to the formula (III):

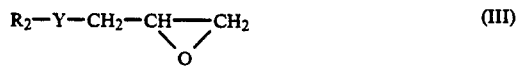

$$R_2-Y-CH_2-CH\underset{O}{\overset{}{\diagdown\diagup}}CH_2 \quad (III)$$

When X denotes oxygen, these reactions are preferably carried out in the presence of a molar excess of the compound of formula (II) relative to the compound of formula (III), it being possible for this excess to reach five times the stoichiometric amount, in the presence of an acid catalyst such as, for example, boron trifluoride, $SnCl_4$ or $ZnCl_2$, or in the presence of an alkaline catalyst such as sodium or potassium, or sodium or potassium methylate, ethylate or tert-butylate.

With acid catalysis, the reaction temperature is between 40° C. and 100° C.; it is preferably between 80° and 180° C. with alkaline catalysis.

When one of the groups X or Y denotes a sulphur atom, the reaction is preferably carried out under alkaline catalysis and with stoichiometric proportions of the compounds of formulae (II) and (III).

The proportion of catalyst used is generally from 0.1 to 3% by weight relative to the weight of the reaction mixture.

Depending on the direction of opening of the epoxide of rormula (III), it is possible to obtain the isomers of the following formulae (Ia) and (Ib):

$$R_1-X-CH_2-\underset{OH}{\overset{}{C}H}-CH_2-Y-R_2 \quad (Ia)$$

$$R_1-X-\underset{CH_2-OH}{\overset{}{C}H}-CH_2-Y-R_2 \quad (Ib)$$

The compounds of formula (I) may be purified, after removal under reduced pressure of the residual compound containing active hydrogen of formula (II), by molecular distillation at approximately $10^{-3}$ mm of mercury (0.13 pascal).

When the starting compound of formula (II) is an alcohol, it is also possible to use, in the context of the invention, the reaction product after simply partial or total removal of the excess alcohol of formula (II), or even the crude reaction product, that is to say retaining all of the excess fatty alcohol of formula (II). In effect, the fatty alcohols of formula (II) used in the context of the preparation of the compounds of formula (I), used according to the invention, are not detrimental to the expected properties of the compounds of formula (I), and they may contribute to the stabilisation and opacification of the detergent compositions.

The compounds of formula (I) in which at least one of the groups X or Y denotes a sulphur atom may be oxidised, according to conventional processes, to sulphoxides which correspond to the formula (IV):

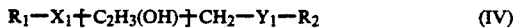

$$R_1-X_1+C_2H_3(OH)+CH_2-Y_1-R_2 \quad (IV)$$

in which $R_1$ and $R_2$ have the same meaning as in the formula (I); $X_1$ denotes an oxygen atom or a sulphoxide group; $Y_1$ denotes an oxygen atom or a methylene or sulphoxide group; at least one of the symbols $X_1$ or $Y_1$ represents a sulphoxide group.

The silicones used according to the invention are, in particular, polyorganosiloxanes which are insoluble in the composition and can take the form of oils, waxes, resins or gums.

The organopolysiloxanes are defined in greater detail in the work by Walter NOLL "Chemistry and Technology of Silicones" (1968) Academie Press. They can be volatile or non-volatile.

When they are volatile, they are selected from those possessing a boiling point of between 60° C. and 260° C., and more especially from:

(i) cyclic silicones containing from 3 to 7 silicon atoms, and preferably 4 to 5. They are, for example, the octamethylcyclotetrasiloxane sold under the name "VOLATILE SILICONE 7207" by UNION CARBIDE or "SILBIONE 70045 V 2" by RHONE POULENC, or the decamethylcyclopentasiloxane sold under the name "VOLATILE SILICONE 7158" by UNION CARBIDE or "SILBIONE 70045 V 5" by RHONE POULENC, as well as mixtures thereof.

Cyclic copolymers of the dimethylsiloxane/methylalkylsiloxane type, such as "SILICONE VOLATILE FZ 3109" sold by the company UNION CARBIDE, of chemical structure:

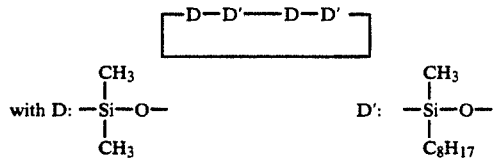

are also mentioned.

Mixtures of cyclic silicones with organic compounds derived from silicon, such as a mixture of octamethylcyclotetrasiloxane and tetratrimethylsilylpentaerythritol (50:50) and a mixture of octamethylcyclotetrasiloxane and 1,1'-oxy-2,2,2',2',3,3'-hexa(trimethylsilyloxy)bis-neopentane may also be mentioned;

(ii) volatile linear silicones having 2 to 9 silicon atoms and possessing a viscosity not exceeding $5 \times 10^{-6}$ m²/s at 25° C. They are, for example, the decamethyltetrasiloxane sold under the name "SH 200" by the company TORAY SILICONE. Silicones belonging to this class are also described in the paper published in Cosmetics and Toiletries, Vol. 91, January 76, p. 27-3-2—TODD & BYERS "Volatile silicone fluids for cosmetics".

Non-volatile silicones are preferably used, and more especially polyalkylsiloxanes, polyarylsiloxanes, polyalkylarylsiloxanes, silicone gums and resins and polyorganosiloxanes modified with organic functional groups, as well as mixtures thereof.

These silicones are more especially selected from polyalkylsiloxanes, among which linear polydimethylsiloxanes containing terminal trimethylsilyl groups and having a viscosity of $5 \times 10^{-6}$ to 2.5 m²/s at 25° C., and preferably $1 \times 10^{-5}$ to 1 m²/s, may be chiefly mentioned.

Among these polyalkylsiloxanes, there may be mentioned, without implied limitation, the following commercial products:

SILBIONE oils of the 47 and 70 047 series marketed by RHONE POULENC, such as, for example, the oil 47 V 500 000;

oils of the 200 series of the company DOW CORNING;

the VISCASIL oils of GENERAL ELECTRIC and some oils of the SF series (SF 96, SF 18) of GENERAL ELECTRIC.

Linear polydimethylsiloxanes containing terminal dimethylsilanol groups, such as oils of the 48 series of the company RHONE POULENC, may also be mentioned.

In this class of polyalkylsiloxanes, the products sold under the names "ABIL WAX 9800 and 9801" by the company GOLDSCHMIDT, which are poly($C_1$-$C_{20}$ alkyl)siloxanes, may also be mentioned.

The polyalkylarylsiloxanes are, in particular, selected from linear and/or branched polydimethylmethylphenylsiloxanes and polydimethyldiphenylsiloxanes of viscosity from $1 \times 10^{-5}$ to $5 \times 10^{-2}$ m²/s at 25° C.

Among these polyalkylarylsiloxanes, there may be mentioned, by way of example, the products marketed under the following names:

SILBIONE oils of the 70 641 series of RHONE POULENC;

oils of the RHODORSIL 70 633 and 763 series of RHONE POULENC;

the oil DC 556 COSMETIC GRADE FLUID of DOW CORNING;

silicones of the PK series of BAYER, such as the product PK 20;

silicones of the PN and PH series of BAYER, such as the products PN 1000 and PH 1000;

some oils of the SF series of GENERAL ELECTRIC, such as SF 1023, SF 1154, SF 1250, SF 1265.

The silicone gums which are usable according to the invention are, in particular, polydiorganosiloxanes having high molecular masses of between 200,000 and 1,000,000, used alone or as a mixture in a solvent. This solvent may be selected from volatile silicones, polydimethylsiloxane (PDMS) oils, polyphenylmethylsiloxane (PPMS) oils, isoparaffins, methylene chloride, pentane, dodecane, tridecane, tetradecane or mixtures thereof.

There may be mentioned, more especially, the following products:

polydimethylsiloxane/methylvinylsiloxane gums,
polydimethylsiloxane/diphenylsiloxane,
polydimethylsiloxane/phenylmethylsiloxane, polydimethylsiloxane/diphenylsiloxane/methylvinylsiloxane.

Products which are more especially usable according to the invention are mixtures such as:

the mixtures formed from a polydimethylsiloxane hydroxylated at the end of the chain (designated dimethiconol according to the nomenclature of the CTFA dictionary) and a cyclic polydimethylsiloxane (designated cyclomethicone according to the nomenclature of the CTFA dictionary), such as the product Q2 1401 sold by the company DOW CORNING;

the mixtures formed from a polydimethylsiloxane gum with a cyclic silicone, such as the product SF 1214 Silicone Fluid of the company GENERAL ELECTRIC; this product is an SE 30 gum corresponding to a dimethicone, having a molecular weight of 500,000, solubilised in the oil SF 1202 Silicone Fluid corresponding to decamethylcyclopentasiloxane;

the mixtures of two PDMS of different viscosities, and more especially of a PDMS gum and a PDMS oil, such as the product SF 1236 of the company GENERAL ELECTRIC. The product SF 1236 is a mixture of an SE 30 gum defined above having a viscosity of 20 $m^2/s$ and an SF 96 oil of viscosity $5 \times 10^{-6}$ $m^2/s$. This product preferably contains 15% of SE 30 gum and 85% of an SF 96 oil.

The organopolysiloxane resins which are usable according to the invention are crosslinked siloxane systems containing the units:

$R_2SiO_{2/2}$, $RSiO_{3/2}$ and $SiO_{4/2}$ in which units R represents a hydrocarbon group possessing 1 to 6 carbon atoms or a phenyl group. Among these products, those which are especially preferred are those in which R denotes a lower alkyl radical or a phenyl radical.

Among these resins, the product sold under the name "DOW CORNING 593" or those sold under the names "SILICONE FLUID SS 4230 and SS 4267" by the company GENERAL ELECTRIC, and which are siloxanes of dimethyl/trimethylsiloxane structure, may be mentioned.

The silicones modified with organic groups which are usable according to the invention are silicones as defined above and containing in their structure one or more organic functional groups bound directly to the siloxane chain or bound via a hydrocarbon radical.

Among these silicones, there may be mentioned the silicones containing:

polyethylenoxy and/or polypropylenoxy groups optionally containing alkyl groups, such as the product designated dimethicone copolyol sold by the company DOW CORNING under the name DC 1248, and the ($C_{12}$ alkyl)methicone copolyol sold by the company DOW CORNING under the name Q2 5200; and the oils SILWET L 722, L 7500, L 77, L 711 of the company UNION CARBIDE;

substituted or unsubstituted amino groups, such as the products sold under the name GP4 Silicone Fluid and GP 7100 by the company GENESEE or the products sold under the names Q2 8220 and DC 929 by the company DOW CORNING. The substituted amino groups are, in particular, $C_1$-$C_4$ aminoalkyl groups;

thiol groups, such as the products sold under the names "GP 72 A" and "GP 71" of GENESEE;

carboxylate groups, as in the products described in Patent EP 186,507 of the company CHISSO CORPORATION;

alkoxy groups, such as the product sold under the name "SILICONE COPOLYMER F-755" by SWS SILICONES and ABIL WAX 2428, 2434 and 2440 by the company GOLDSCHMIDT;

hydroxyl groups, such as the polyorganosiloxanes containing a hydroxyalkyl function described in French Patent Application FR-A-85/16,334, corresponding to the formula (V):

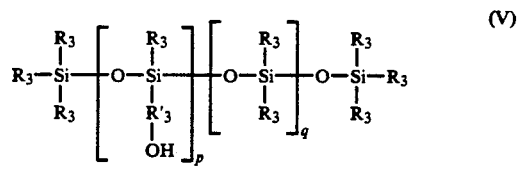

in which the radicals $R_3$, which may be identical or different, are selected from methyl and phenyl radicals, at least 60 mol % of the radicals $R_3$ denoting methyl; the radical $R'_3$ is a divalent $C_2$-$C_{18}$ carbon/hydrogen-based alkylene unit; p is between 1 and 30 inclusive; q is between 1 and 150 inclusive;

acyloxyalkyl groups, such as, for example, the polyorganosiloxanes described in French Patent Application FR-A-88/17,433 and corresponding to the formula (VI)

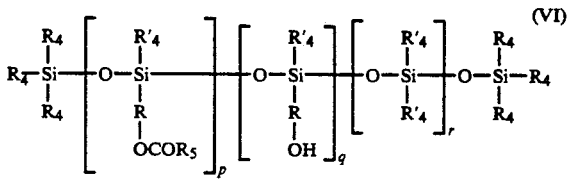

in which:

$R_4$ denotes a methyl, phenyl, —$OCOR_5$ or hydroxyl group, it being possible for only one of the radicals $R_4$ per silicon atom to be OH;

$R'_4$ denotes methyl or phenyl; a molar proportion of at least 60% of all the radicals $R_4$ and $R'_4$ denoting methyl;

$R_5$ denotes $C_8$-$C_{20}$ alkyl or alkenyl;

R denotes a divalent, linear or branched $C_2$-$C_{18}$ carbon/hydrogen-based alkylene radical;

r is between 1 and 120 inclusive;

p is between 1 and 30;

q is equal to 0 or is less than 0.5 p, p+q being between 1 and 30; the polyorganosiloxanes of formula (VI) can contain groups

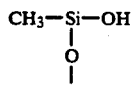

in proportions not exceeding 15% of the sum p+q+r.

The compounds of formula (VI) may be prepared by esterification of polyorganosiloxanes containing a hydroxyalkyl function of formula (V) above.

The esterification is performed in a known manner with an acid $R_5COOH$ or the acid anhydride at a temperature of between 100° and 250° C., optionally in the presence of a catalyst such as aluminum chloride or zinc chloride or a strong acid such as hydrochloric acid or sulphuric acid.

It is also possible to perform a transesterification by heating a methyl ester of formula $R_5COOCH_3$ and a diorganopolysiloxane of formula (V) to 100°-150° C. in the presence of an acid catalyst such as para-toluenesulphonic acid or an acid earth of the montmorillonite type, such as, for example, the product sold under the name "KATALYSATOR KSF/0" by the company SUD-CHEMIE;

anionic groups of the carboxyl type, such as alkylcarboxyl groups, for example those present in the product X-22-3701E of the company SHIN-ETSU; 2-hydroxyalkysulphonate groups; 2-hydroxyalkyl thiosulphate groups, such as the products sold by the company GOLDSCHMIDT under the names "ABIL S 201" and "ABIL S 255".

hydroxyacylamino groups, such as the polyorganosiloxanes described in Application EP 342,834. For example, the product Q2-8413 of the company DOW CORNING may be mentioned.

Especially preferred polyorganosiloxanes according to the invention are:

non-volatile silicones selected from the family of linear polyalkylsiloxanes containing terminal trimethylsilyl groups, such as the oils having a viscosity of between 0.2 and 2.5 m²/s at 25° C. of the SILBIONE 70047 and 47 series, and more especially the oil 47 V 500 000, which are marketed by the company RHONE POULENC, or polyalkylarylsiloxanes such as the oil SILBIONE 70641 V 200 marketed by the company RHONE POULENC;

mixtures of organosiloxanes and cyclic silicones, such as the product Q2 1401 sold by the company DOW CORNING and the product SF 1214 sold by the company GENERAL ELECTRIC;

mixtures of two PDMS of different viscosities, in particular of a gum and an oil, such as the product SF 1236 sold by the company GENERAL ELECTRIC;

the organopolysiloxane resin sold under the name DOW CORNING 593.

The surfactants used in the washing compositions according to the invention are selected from anionic, amphoteric, zwitterionic and nonionic surfactants or mixtures thereof having detergent properties.

Among these anionic surfactants, there may be mentioned more especially: the alkali metal salts, ammonium salts, amine salts, amino alcohol salts and magnesium salts of the following compounds:

alkyl sulphates, alkyl ether sulphates, alkylamido ether sulphates, alkylaryl polyether sulphates, monoglyceride sulphates;

alkylsulphonates, alkylamide sulphonates, alkylarylsulphonates, olefin sulphonates, paraffin sulphonates;

alkylsulphosuccinates, alkyl ether sulphosuccinates, alkylamide sulphosuccinates;

alkylsulphosuccinamates;

alkylsulphoacetates;

alkyl phosphates, alkyl ether phosphates;

acylsarcosinates, acylisethionates, N-acyltaurinates.

The alkyl or acyl radical of these various compounds generally consists of a carbon chain containing from 12 to 20 carbon atoms.

Among anionic surfactants, there may also be mentioned: the salts of fatty acids such as oleic, ricinoleic, palmitic and stearic acids; the acids of coconut oil or of hydrogenated coconut oil; and acyllactylates in which the acyl radical contains 8 to 20 carbon atoms.

Other anionic surfactants consist of polyoxyalkylenated carboxylic ether-acids of formula:

$$R_6—(OC_3H_6)_p—(OC_2H_4)_n—OCH_2COOA \quad \text{(VII)}$$

in which:
R$_6$ denotes a linear or branched C$_8$-C$_{22}$ alkyl or alkenyl radical or a mixture of such radicals, a (C$_8$-C$_9$ alkyl)phenyl radical or R$_7$CONH—CH$_2$—CH$_2$— with R$_7$ denoting a linear or branched C$_{11}$-C$_{21}$ alkyl or alkenyl radical;
n is an integer or decimal number between 2 and 24,
p is an integer or decimal number between 0 and 6,
A denotes a hydrogen atom or alternatively Na, K, Li, ½ Mg or a monoethanolamine, ammonium or triethanolamine residue.

The polyoxyalkylenated carboxylic ether-acids which are usable according to the invention are preferably selected from the compounds of formula (VII) in which R$_6$ denotes a C$_{10}$-C$_{18}$ alkyl or oleyl radical or a mixture of such radicals, or a nonylphenyl or octylphenyl radical, A denotes a hydrogen or sodium atom and p=0.

It is preferable to use the commercial products sold by the company CHEM Y under the names AKYPO or by the company SANDOZ under the names "SANDOPAN".

Among nonionic surfactants, there may be mentioned more especially: polyethoxylated, polyoxypropylenated or polyglycerolated alcohols, alkylphenols and fatty acids having a fatty chain containing 8 to 18 carbon atoms; the number of ethylene oxide or propylene oxide groups being between 2 and 50 and the number of glycerol groups being between 2 and 30.

There may also be mentioned copolymers of ethylene and propylene oxides, condensates of ethylene and propylene oxides with fatty alcohols, polyethoxylated fatty amides (preferably containing 2 to 30 moles of ethylene oxide), polyethoxylated fatty amines (preferably having 2 to 30 moles of ethylene oxide), ethanolamides, fatty acid esters of sorbitan, oxyethylenated (preferably with 2 to 30 moles of ethylene oxide) or otherwise, fatty acid esters of polyethylene glycol, phosphoric triesters, fatty acid esters of sucrose, alkylpolyglycosides and oxides of fatty amines such as the oxides of alkylamines or of N-acylamidopropylmorpholine.

Preferred oxyethylenated or polyglycerolated fatty alcohols are oxyethylenated oleyl alcohol containing 10 moles of ethylene oxide, oxyethylenated lauryl alcohol containing 12 moles of ethylene oxide, oxyethylenated nonylphenol containing 9 moles of ethylene oxide and polyglycerolated oleyl alcohol containing 4 moles of glycerol.

Other compounds belonging to this class are compounds corresponding to the formulae (VIII) to (X) below and/or among the compounds prepared according to the processes described below:

a) the compounds of formula:

$$R_8O—(CH_2—\underset{\underset{CH_2OH}{|}}{CH}—O)_{\overline{m}}H \quad \text{(VIII)}$$

in which R$_8$ denotes an alkyl radical having 10 to 14 carbon atoms or a mixture of such radicals and m is an integral or decimal statistical value from 2 to 10 and preferably from 3 to 6. These compounds may be prepared according to the process described in Patent FR-A-1,477,048;

b) the derivatives of formula:

$$R_9-CONH-CH_2-CH_2-O-CH_2-CH_2-O(CH_2-CHOH-CH_2-O)_{\overline{n}}H \quad (IX)$$

in which $R_9$ denotes an alkyl and/or alkenyl radical having 11 to 17 carbon atoms or a mixture of such radicals and n denotes an integral or decimal statistical value from 1 to 5 and preferably 1.5 to 4. These compounds of formula (IX) may be prepared according to the process described in French Patent FR-A-2,328,763;

c) the compounds of formula:

$$R_{10}-CHOH-CH_2-O-(CH_2-CHOH-CH_2-O)_{\overline{p}}H \quad (X)$$

in which $R_{10}$ denotes an aliphatic, cycloaliphatic or arylaliphatic radical preferably having 7 to 21 carbon atoms and mixtures thereof; the aliphatic chains denoting, in particular, alkyl chains which can contain from 1 to 6 ether, thioether and/or hydroxymethylene groups and p has a statistical value from 2 to 10 inclusive.

These compounds are prepared by alkali-catalysed condensation of 2 to 10 moles, and preferably 2.5 to 6 moles, of glycidol with a $C_9-C_{23}$ alpha-diol or a mixture of such alpha-diols at a temperature of 120°–180° C., and preferably 140° to 160° C., the glycidol being added slowly according to the preparation process described in Patent FR-A-2,091,516;

d) the compounds prepared by acid-catalysed condensation of 2 to 10, and preferably 2.5 to 6, moles of glycidol per mole of alcohol or alpha-diol containing 10 to 14 carbon atoms, at a temperature of 50° to 120° C., the glycidol being added slowly to the alcohol or alpha-diol. The process for preparing these compounds is described in Patent FR-A-2,169,787;

e) the poly(hydroxypropyl ether) compounds prepared by polyaddition of glycerol monochlorohydrin to an organic compound containing a polyhydroxylated fatty chain in the presence of a strong base, removing the water by distillation as it forms, which are described, more especially, in Patent FR-A-2,574,786.

Among nonionic surfactants of the poly(hydroxypropyl ether) family described in sections (a), (b), (c), (d) and (e) above, preferred compounds are represented by the formulae:

$$C_{12}H_{25}O-(CH_2-\underset{\underset{CH_2OH}{|}}{CH}-O)_{\overline{4.2}}H \quad (XI)$$

$$R_8O-(CH_2-\underset{\underset{CH_2OH}{|}}{CH}-O)_{\overline{3.75}}H \quad (XII)$$

where $R_8$ denotes a mixture of $C_{10}H_{21}$ and $C_{12}H_{25}$ alkyl radicals;

the compounds prepared by alkali-catalysed condensation of 3.5 moles of glycidol with an alpha-diol having 12 carbon atoms, according to the process described in Patent FR-A-2,091,516;

and the compounds corresponding to the formula:

$$R_{10}-CONH-CH_2-CH_2-O-CH_2-CH_2-O-(CH_2-CHOH-CH_2-O)_{\overline{3.5}}H \quad (XIII)$$

where $R_{10}$ denotes a mixture of radicals comprising the following alkyl and alkenyl radicals: $C_{11}H_{23}$, $C_{13}H_{27}$, the radicals derived from coconut fatty acids and radicals derived from oleic acid;

the compounds prepared by condensation of 3.5 moles of glycidol with a mixture of $C_{11}-C_{14}$ alpha-diols, as described in Patent FR-A-2,091,516, and the nonionic poly(hydroxypropyl ether) surfactant obtained by condensation of glycerol monochlorohydrin (2.5 moles) with 1,2-dodecanediol in the presence of sodium hydroxide, are especially preferred.

Among amphoteric and zwitterionic surfactants which can be used, there may be mentioned, by way of example:

1. derivatives of secondary or tertiary aliphatic amines in which the aliphatic radical is a linear or branched chain containing from 8 to 18 carbon atoms and which contains at least one anionic carboxyl, sulphonate, sulphate, phosphate or phosphonate group conferring solubility in water;
2. alkylbetaines, sulphobetaines, amidobetaines or amidosulphobetaines.

Among these compounds, the products sold under the name "MIRANOL" described, in particular, in Patents U.S. Pat. Nos. 2,528,378 and 2,781,354 and classified in the CTFA dictionary (3rd edition, 1982) under the name "AMPHOCARBOXYGLYCINATES and AMPHOCARBOXYPROPIONATES" may be mentioned more especially.

These products possess the following structures: for the AMPHOCARBOXYGLYCINATES:

$$R_{11}-\underset{\underset{O}{\|}}{C}-NH-CH_2-CH_2-\overset{+}{N}\diagdown_{CH_2COOH}^{CH_2CH_2OH}\!\!\!\!\diagup^{CH_2COO^-} \quad (XIV)$$

in which $R_{11}$ denotes an alkyl radical derived from coconut or a heptyl, nonyl or undecyl radical;

for the AMPHOCARBOXYPROPIONATES:

$$R_{12}-\underset{\underset{O}{\|}}{C}-NH-CH_2-CH_2-N\diagdown_{(CH_2)_n-Y}^{CH_2CH_2O-X} \quad (XV)$$

n=1 or 2;
X denotes —$CH_2CH_2COOH$ or hydrogen;
Y denotes —COOH or the radical $$-\underset{\underset{OH}{|}}{CH}-CH_2SO_3H$$

$R_{12}$ denotes an alkyl radical derived from coconut, a $C_7$, $C_9$, $C_{11}$ or $C_{13}$ alkyl radical, a $C_{17}$ alkyl radical and its iso form, an unsaturated $C_{17}$ radical or an alkyl radical derived from linseed oil.

The alkylbetaines are preferably chosen from ($C_{10}-C_{20}$ alkyl)betaines.

In the compositions according to the invention, mixtures of surfactants are preferably used, and especially mixtures of anionic surfactants and amphoteric, zwitterionic or nonionic surfactants. An especially preferred mixture is a mixture consisting of an anionic surfactant and a zwitterionic surfactant.

It is preferable to use an anionic surfactant selected from sodium, triethanolamine or ammonium ($C_{12}$-$C_{14}$ alkyl) sulphates, oxyethylenated sodium ($C_{12}$-$C_{14}$ alkyl) ether sulphates containing 2.2 moles of ethylene oxide, sodium cocoylisethionate and sodium ($C_{14}$-$C_{16}$ α-olefin) sulphonate and mixtures thereof with either an amphoteric surfactant such as the amphocarboxyglycinate defined by the formula (XIV) above in which $R_{11}$ denotes an alkyl radical derived from coconut, designated cocoamphocarboxyglycinate, sold by the company MIRANOL under the trade name "MIRANOL C2M CONC" in aqueous solution containing 38% of active substance;

or a zwitterionic surfactant such as the laurylbetaine sold under the name "DEHYTON AB 30" in aqueous solution containing 32% of AS by the company HENKEL.

The silicones are used in the compositions according to the invention in proportions preferably of between 0.05 and 20%, and preferably of between 0.1 and 10%, by weight relative to the total weight of the composition.

The alcohols containing ether and/or thioether or sulphoxide group(s) corresponding to the formula (I) or to the formula (IV), used according to the invention, are present in sufficient proportions to provide for the homogeneity, thickening and opalescence of the compositions, and preferably in proportions of between 0.1 and 10% relative to the total weight of the composition, and especially between 0.5 and 5%.

The surfactants are used in the compositions according to the invention in sufficient proportions to impart a detergent character to the composition, and which are preferably between 5 and 50% relative to the total weight of the composition, and especially between 8 and 35%.

The pH of these compositions is generally between 3 and 9, and more especially between 4 and 8.

The aqueous medium can consist of only water, or of a mixture of water and a cosmetically acceptable solvent such as a $C_1$-$C_4$ lower alcohol, for example ethanol, isopropanol or n-butanol, alkylene glycols, for example ethylene glycol, or glycol ethers.

The compositions according to the invention can contain, in addition to the combination defined above, viscosity regulators such as electrolytes, hydrotropes or other thickening agents. Sodium chloride, sodium xylenesulphonate, scleroglucans, xanthan gums, coconut acid alkanolamides, and alkanolamides of alkyl ether carboxylic acid which are optionally oxyethylenated with up to 5 moles of ethylene oxide, such as the product sold under the name "AMINOL A15" by the company CHME Y may be mentioned in particular. These viscosity regulators are used in the compositions according to the invention in proportions which can range up to 10% by weight relative to the total weight of the composition.

The compositions according to the invention can also contain up to 3% of pearlescence or opacifying agents which are well known in the prior art, such as, for example, sodium or magnesium palmitates, sodium or magnesium stearates and hydroxystearates or ethylene glycol monostearate or distearate.

The compositions according to the invention can optionally contain, in addition, other agents having the effect of improving the cosmetic properties of the hair or the skin without, however, impairing the stability of the compositions. Cationic surfactants, anionic or nonionic or cationic and amphoteric polymers or optionally quaternised proteins may be mentioned in this connection.

The cationic polymers are selected from polymers containing primary, secondary, tertiary and/or quaternary amine groups forming part of the polymer chain or directly linked to the latter, having a molecular weight of between 500 and approximately 5,000,000.

There may be mentioned, without implied limitation: quaternary polyammonium polymers such as those described in Application EP-A-122,324 or in French Patents 2,333,012, 2,270,846, 2,270,851, 2,471,777, 2,316,271 and 2,331,323 or U.S. Pat. No. 4,157,388.

Especially preferred quaternary polyammonium compounds are those containing the units:

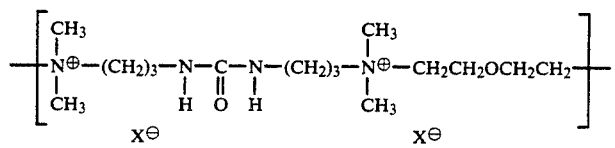

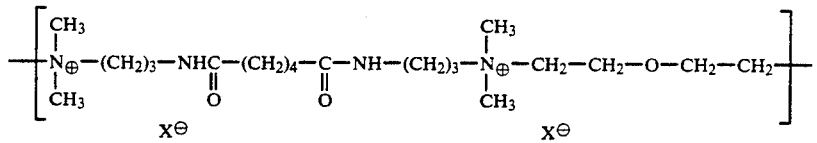

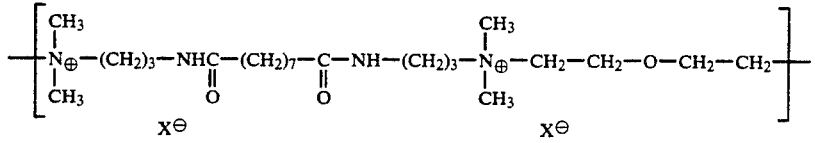

These quaternary polyammonium compounds are sold under the name MIRAPOL A15, MIRAPOL AD1, MIRAPOL AZ1 or MIRAPOL 175 by the company MIRANOL.

Cationic polysaccharides such as those described in U.S. Pat. Nos. 3,589,578 and 4,031,307, for example the product marketed under the name JAGUAR C 13S by MEYHALL may also be mentioned as cationic polymers.

By way of an amphoteric polymer, there may be mentioned:

polymers preferably containing approximately 60 to approximately 99% of units derived from a diallyldialkylammonium monomer in which the alkyl groups contain from 1 to 18 carbon atoms, and preferably approximately 1 to approximately 40% of units derived from monomers selected from acrylic and methacrylic acids. The average molecular weight of these polymers, determined by gel permeation chromatography, is between 50,000 and 1,000,000.

Preferred polymers are polymers of dimethyl-diallyl- or diethyldiallylammonium and acrylic acid such as the product marketed under the name MERQUAT 280 by the company MERCK;

polymers derived from chitosan, such as those described in FR 2,137,684 and containing units corresponding to the formulae:

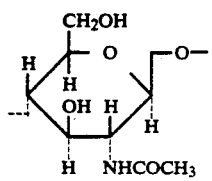 (A)

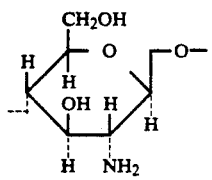 (B)

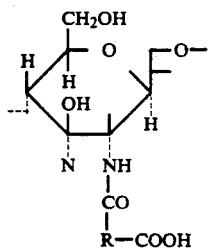 (C)

in which the unit A is present in proportions from 0 to 30% by weight, the unit B from 5 to 50% by weight and the unit C in proportions from 30 to 90% by weight; R represents a linear or branched alkylene group containing from 2 to 5 carbon atoms.

Preferred polymers contain from 0 to 20% of units A, 40 to 50% of units B and 40 to 50% of units C, and R denotes —CH$_2$—CH$_2$—.

The compositions can also contain foam synergists such as C$_{10}$-C$_{18}$ 1,2-alkanediols or fatty alkanolamides derived from mono- or diethanolamine.

These compositions can also contain various adjuvants used commonly in cosmetics, such as fragrances, preservatives, sequestering agents, foam stabilisers and acidifying or alkalinising agents which are well known in cosmetics.

The compositions according to the invention are preferably used as shampoos for washing and conditioning the hair, and they are applied in this case to the wet hair in quantities which are effective for washing it, this application being followed by a rinse with water.

The compositions according to the invention are also usable as shower gels for washing the hair and the skin, in which case they are applied to the skin and the wet hair and are rinsed after application.

The examples which follow are intended as illustrations of the invention, no limitation of the latter being implied.

EXAMPLE 1

A shampoo of opaque appearance and having the following composition is prepared:

| | |
|---|---|
| Oxyethylenated sodium (C$_{12}$-C$_{14}$ alkyl) ether sulphate containing 2.2 moles of ethylene oxide, sold at a concentration of 28% of AS | 14 g AS |
| Laurylbetaine sold by the company HENKEL under the trade name "DEHYTON AB 30" in aqueous solution containing 32% of AS | 2.6 g AS |
| Sodium cocoylisethionate sold under the name "ARLATONE SCI Prilled" by the company ICI | 6 g |
| Oxyethylenated linear C$_{12}$-C$_{14}$ alcohol containing 3 moles of ethylene oxide | 10 g |
| Oil 47 V 500000 sold by the company RHONE POULENC | 3 g |
| Compound of formula (I) in which | |
| R$_1$ = C$_{12}$H$_{25}$<br>X = O, Y = CH$_2$<br>R$_2$ = C$_{12}$H$_{25}$/C$_{14}$H$_{29}$ (50:50 in moles)<br>prepared by reaction of 3 moles of alcohol with one mole of epoxide followed by distillation of the excess alcohol | 3 g |
| Preservative, fragrance qs | |
| natural pH | 5.7 |
| Water qs | 100 g |

Hair washed with this foaming and strongly detergent shampooing composition combs easily and is shiny and soft to the touch.

EXAMPLE 2

A shampoo of opaque appearance and having the following composition is prepared:

| | |
|---|---|
| Oxyethylenated sodium (C$_{12}$-C$_{14}$ alkyl) ether sulphate containing 2.2 moles of ethylene oxide, sold at a concentration of 28% of AS | 14 g AS |
| Laurylbetaine sold by the company HENKEL under the trade name "DEHYTON AB 30" in aqueous solution containing 32% of AS | 2.6 g AS |
| Sodium cocoylisethionate sold under the name "ARLATONE SCI Prilled" by the company ICI | 6 g |
| Oil 47 V 500000 sold by the company RHONE POULENC | 3 g |
| Compound of formula (I) in which | |
| R$_1$ = C$_{14}$H$_{29}$, R$_2$ = C$_{12}$H$_{25}$<br>X = O, Y = CH$_2$<br>prepared by reaction of 3 moles of alcohol with one mole of epoxide followed by distillation of the excess alcohol and distillation of the compound of formula (I) | 2.5 g |
| Oxyethylenated monoethanolamide of (C$_{13}$-C$_{15}$ alkyl) ether carboxylic acid containing 2 moles of ethylene oxide, sold under the name "AMINOL A 15" by the company CHEM Y | 2 g |
| Preservative, fragrance qs | |
| natural pH | 5.2 |
| water qs | 100 g |

Hair washed with this foaming and strongly detergent shampooing composition combs easily and is shiny and soft to the touch.

EXAMPLE 3

A shampoo of opaque appearance and having the following composition is prepared:

| | |
|---|---|
| Oxyethylenated sodium ($C_{12}$-$C_{14}$ alkyl) ether sulphate containing 2.2 moles of ethylene oxide, sold at a concentration of 28% of AS | 14 g AS |
| Lauryl alcohol monosulphosuccinate disodium salt, sold in aqueous solution containing 40% of AS by the company ZSCHIMMER and SCHWARZ under the name "SETACIN F Special Paste" | 2.4 g AS |
| Laurylbetaine sold by the company HENKEL under the trade name "DEHYTON AB 30" in aqueous solution containing 32% of AS | 2.6 g AS |
| Oil 47 V 500000 sold by the company RHONE POULENC | 3 g |
| Compound of formula (I) in which $R_1 = C_{16}H_{33}$, $R_2 = C_{14}H_{29}$ $X = O$, $Y = CH_2$ prepared by reaction of 3 moles of alcohol with one mole of epoxide, used in the crude state | 2.5 g |
| Oxyethylenated monoethanolamide of ($C_{13}$-$C_{15}$ alkyl) ether carboxylic acid containing 2 moles of ethylene oxide, sold under the name "AMINOL A 15" by the company CHEM Y | 3 g |
| Sodium chloride | 0.2 g |
| Preservative, fragrance qs | |
| natural pH | 5.4 |
| water qs | 100 g |

Hair washed with this foaming and strongly detergent shampooing composition combs easily and is shiny and soft to the touch.

EXAMPLE 4

A shampoo of the following composition is prepared:

| | |
|---|---|
| Polysiloxane containing a hydroxyacylamino function, sold under the name Q2-8413 by the company DOW CORNING | 4 g |
| Quaternised hydroxyethylcellulose sold under the name JR 400 by the company UNION CARBIDE | 0.1 g |
| Oxyethylenated sodium lauryl ether sulphate containing 2 moles of ethylene oxide, at a concentration of 28% of AS | 15 g AS |
| Cocoylbetaine at a concentration of 32% of As | 2.4 g AS |
| Ethylene glycol distearate | 2 g |
| Compound of formula $C_{16}H_{33}$—O—$C_2H_3$(OH)—$CH_2$—$C_{14}H_{29}$ prepared by reaction of 3 moles of alcohol with one mole of epoxide, used in the crude state | 2.5 g |
| Triethanolamine qs pH | 7.4 |
| water qs | 100 g |

EXAMPLE 5

A pearlescent shower gel of the following composition is prepared:

| | |
|---|---|
| Oxyethylenated sodium ($C_{12}$-$C_{14}$ alkyl) ether sulphate containing 2.2 moles of ethylene oxide, sold at a concentration of 28% of AS | 16.8 g AS |
| Cocoylbetaine containing 32% of AS | 2.56 g AS |
| Oil 47 V 500000 sold by the company RHONE POULENC | 2.5 g |
| Compound of formula (I) in which: $R_1 = C_{16}H_{33}$, $R_2 = C_{14}H_{29}$ $X = O$, $Y = CH_2$ prepared by reaction of 3 moles of alcohol with one mole of epoxide, used in the crude state | 2.5 g |
| Coconut diethanolamide | 2.5 g |
| Copolymer of diallyldimethylammonium chloride and acrylic acid, sold under the name MERQUAT 280 by the company CALGON at a concentraion of 35% of AS | 0.18 g AS |
| Preservative, fragrance qs | |
| natural pH | 6.5 |
| water qs | 100 g |

EXAMPLE 6

A pearlescent gel shampoo of the following composition is prepared:

| | |
|---|---|
| Oxyethylenated sodium ($C_{12}$-$C_{14}$ alkyl) ether sulphate containing 2.2 moles of ethylene oxide, sold at a concentration of 28% of AS | 16.8 g AS |
| Cocoylbetaine containing 32% of AS | 2.56 g AS |
| Trimethylsilylamodimethicone sold as a cationic emulsion containing 35% of AS under the name DC 929 by the company DOW CORNING | 2.75 g AS |
| Compound of formula (I) in which: $R_1 = R_2 = C_{16}H_{33}$ $X = Y = O$ | 2.5 g |
| Coconut acid monoisopropanolamide | 1.5 g |
| Preservative, fragrance qs | |
| natural pH | 6.5 |
| water qs | 100 g |

EXAMPLE 7

A pearlescent gel shampoo of the following composition is prepared:

| | |
|---|---|
| Oxyethylenated sodium ($C_{12}$-$C_{14}$ alkyl) ether sulphate containing 2.2 moles of ethylene oxide, sold at a concentration of 28% of AS | 16.8 g AS |
| Cocoylbetaine containing 32% of AS | 2.56 g AS |
| PDMS containing a gamma-hydroxypropyl function, of formula | 2.75 g |

$$CH_3-\underset{\underset{CH_3}{|}}{\overset{\overset{CH_3}{|}}{Si}}-\left[O-\underset{\underset{(CH_2)_3}{|} \\ OH}{\overset{\overset{CH_3}{|}}{Si}}\right]_{1.5}-\left[O-\underset{\underset{CH_3}{|}}{\overset{\overset{CH_3}{|}}{Si}}\right]_{115}-O-\underset{\underset{CH_3}{|}}{\overset{\overset{CH_3}{|}}{Si}}-CH_3$$

$M_n = 9,000$

| | |
|---|---|
| Compound of formula (I) in which: $R_1 = C_{16}H_{33}$, $R_2 = C_{14}H_{29}$ $X = O$, $Y = CH_2$ prepared by reaction of 3 moles of alcohol with one mole of epoxide, used in the crude state | 2.5 g |
| Coconut acid monoisopropanolamide | 0.5 g |
| Preservative, fragrance qs | |
| natural pH | 6.5 |
| Water qs | 100 g |

EXAMPLE 8

A pearlescent gel shampoo of the following composition is prepared:

| | |
|---|---|
| Oxyethylenated ammonium ($C_{12}$–$C_{14}$ alkyl) ether sulphate containing 3 moles of ethylene oxide, sold at a concentration of 25% of AS | 11.5 g AS |
| Ammonium ($C_{12}$–$C_{14}$ alkyl) sulphate sold at a concentration of 30% of As | 6 g AS |
| Cocoylbetaine containing 32% of AS | 2.56 g AS |
| Oil 47 V 500000 sold by the company RHONE POULENC | 1 g |
| Compound of formula (I) in which: | |
| $R_1 = C_{16}H_{33}$, $R_2 = C_{14}H_{29}$ $X = O$, $Y = CH_2$ prepared by reaction of 3 moles of alcohol with one mole of epoxide, used in the crude state | 3 g |
| Oxyethylenated monoethanolamide of ($C_{13}$–$C_{15}$ alkyl) ether carboxylic acid containing 2 moles of ethylene oxide, sold under the name AMINOL A15 by the company CHEM Y | 1.5 g |
| Hydroxypropylated and quaternised guar gum, sold under the name JAGUAR C-13 S by the company MEYHALL | 0.25 g |
| Preservative, fragrance qs | |
| Water qs | 100 g |

EXAMPLE 9

A shower gel of the following composition is prepared:

| | |
|---|---|
| Oxyethylenated sodium ($C_{12}$–$C_{14}$ alkyl) ether sulphate containing 2.2 moles of ethylene oxide, sold at a concentration of 28% of AS | 16.8 g AS |
| Cocoylbetaine containing 32% of AS | 2.56 g AS |
| Dimethicone copolyol sold under the name SILWETT L 722 by the company UNION CARBIDE | 10 g |
| Compound of formula (I) in which: | |
| $R_1 = C_{16}H_{33}$, $R_2 = C_{14}H_{29}$ $X = O$, $Y = CH_2$ prepared by reaction of 3 moles of alcohol with one mole of epoxide, used in the crude state | 2.5 g |
| Coconut acid monoisopropanolamide | 1 g |
| Preservative, fragrance qs | |
| natural pH | 6.3 |
| Water qs | 100 g |

EXAMPLE 10

A shampoo of the following composition is prepared:

| | |
|---|---|
| Oxyethylenated sodium ($C_{12}$–$C_{14}$ alkyl) ether sulphate containing 2.2 moles of ethylene oxide, sold at a concentration of 28% of AS | 16.8 g AS |
| Cocoylbetaine containing 32% of AS | 2.56 g AS |
| Dimethicone copolyol sold under the name SILWETT L 722 by the company UNION CARBIDE | 3 g |
| Compound of formula (I) in which: | |
| $R_1 = C_{16}H_{33}$, $R_2 = C_{14}H_{29}$ $X = O$, $Y = CH_2$ prepared by reaction of 3 moles of alcohol with one mole of epoxide, used in the crude state | 6 g |
| Preservative, fragrance qs | |
| natural pH | 6.5 |
| Water qs | 100 g |

EXAMPLE 11

A shampoo of the following composition is prepared:

| | |
|---|---|
| Oxyethylenated sodium ($C_{12}$–$C_{14}$ alkyl) ether sulphate containing 2.2 moles of ethylene oxide, sold at a concentration of 28% of AS | 16.8 g AS |
| Cocoylbetaine containing 32% of AS | 2.56 g AS |
| Dimethicone copolyol sold under the name SILWETT L 722 by the company UNION CARBIDE | 3 g |
| Compound of formula (I) in which: | |
| $R_1 = C_{16}H_{33}$, $R_2 = C_{14}H_{29}$ $X = O$, $Y = CH_2$ prepared by reaction of 3 moles of alcohol with one mole of epoxide, used in the crude state | 0.5 g |
| Coconut acid monoisopropanolamide | 1.5 g |
| Cetyl alcohol | 2 g |
| Preservative, fragrance qs | |
| natural pH | 6.8 |
| Water qs | 100 g |

EXAMPLE 12

A shower gel of the following composition is prepared:

| | |
|---|---|
| Oxyethylenated sodium ($C_{12}$–$C_{14}$ alkyl) ether sulphate containing 2.2 moles of ethylene oxide, sold at a concentration of 28% of AS | 16.8 g AS |
| Cocoylbetaine containing 32% of AS | 2.56 g AS |
| PDMS containing a gamma-hydroxypropyl function, of formula | 7.5 g |

$$CH_3-\underset{\underset{CH_3}{|}}{\overset{\overset{CH_3}{|}}{Si}}-\left[O-\underset{\underset{(CH_2)_3}{\underset{|}{OH}}}{\overset{\overset{CH_3}{|}}{Si}}\right]_{1.5}-\left[O-\underset{\underset{CH_3}{|}}{\overset{\overset{CH_3}{|}}{Si}}\right]_{115}-O-\underset{\underset{CH_3}{|}}{\overset{\overset{CH_3}{|}}{Si}}-CH_3$$

$M_n = 9{,}000$

| | |
|---|---|
| Compound of formula (I) in which: $R_1 = C_{16}H_{33}$, $R_2 = C_{14}H_{29}$ $X = O$, $Y = CH_2$ prepared by reaction of 3 moles of alcohol with one mole of epoxide, used in the crude state | 2.5 g |
| Coconut acid monoisopropanolamide | 3 g |
| Preservative, fragrance qs | |
| natural pH | 7.4 |
| Water qs | 100 g |

EXAMPLE 13

A shower gel of the following composition is prepared:

| | |
|---|---|
| Oxyethylenated sodium ($C_{12}$–$C_{14}$ alkyl) ether sulphate containing 2.2 moles of ethylene oxide, sold at a concentration of 28% of AS | 16.8 g AS |
| Cocoylbetaine containing 32% of AS | 2.56 g AS |
| Polydimethyldiphenylsiloxane sold under the name SILBIONE HILE 70641V200 by the company RHONE POULENC | 10 g |
| Compound of formula (I) in which: | |

| -continued | |
|---|---|
| $R_1 = C_{16}H_{33}$, $R_2 = C_{14}H_{29}$<br>$X = O$, $Y = CH_2$<br>prepared by reaction of 3 moles of<br>alcohol with one mole of epoxide, used<br>in the crude state | 2.5 g |
| Coconut acid monoisopropanolamide | 3 g |
| Preservative, fragrance qs | |
| natural pH | 7.3 |
| Water qs | 100 g |

EXAMPLE 14

A shampoo of the following composition is prepared:

| | |
|---|---|
| Oxyethylenated sodium ($C_{12}$-$C_{14}$ alkyl) ether sulphate containing 2.2 moles of ethylene oxide, sold at a concentration of 28% of AS | 16.8 g AS |
| Cocoylbetaine containing 32% of AS | 2.56 g AS |
| Polydimethyldiphenylsiloxane sold under the name SILBIONE HILE 70641V200 by the company RHONE POULENC | 3 g |
| Compound of formula (I) in which: | |
| $R_1 = C_{16}H_{33}$, $R_2 = C_{14}H_{29}$<br>$X = O$, $Y = CH_2$<br>prepared by reaction of 3 moles of<br>alcohol with one mole of epoxide, used<br>in the crude state | 6 g |
| Coconut acid monoisopropanolamide | 2 g |
| Preservative, fragrance qs | |
| natural pH | 7.2 |
| Water qs | 100 g |

EXAMPLE 15

A shampoo of the following composition is prepared:

| | |
|---|---|
| Oxyethylenated sodium ($C_{12}$-$C_{14}$ alkyl) ether sulphate containing 2.2 moles of ethylene oxide, sold at a concentration of 28% of AS | 16.8 g AS |
| Cocoylbetaine containing 32% of AS | 2.56 g AS |
| PDMS containing a gamma-hydroxypropyl function, of formula | 3 g |

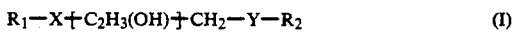

$M_n = 9,000$

| | |
|---|---|
| Compound of formula (I) in which:<br>$R_1 = C_{16}H_{33}$, $R_2 = C_{14}H_{29}$  $X = O$, $Y = CH_2$<br>prepared by reaction of 3 moles of alcohol with<br>one mole of epoxide, used in the crude state | 0.5 g |
| Coconut acid monoisopropanolamide | 2 g |
| Preservative, fragrance qs | |
| natural pH | 7.1 |
| Water qs | 100 g |

EXAMPLE 16

A shampoo of the following composition is prepared:

| | |
|---|---|
| Oxyethylenated sodium ($C_{12}$-$C_{14}$ alkyl) ether sulphate containing 2.2 moles of ethylene oxide, sold at a concentration of 28% of AS | 14 g AS |

| -continued | |
|---|---|
| Cocoylbetaine containing 32% of AS | 1.6 g AS |
| Oil 47 V 500000 sold by the company RHONE POULENC | 2 g |
| Compound of formula (I) in which: | |
| $R_1 = R_2 = C_{12}H_{25}$<br>$X = S$, $Y = CH_2$ | 2.5 g |
| Coconut diethanolamide | 3 g |
| Preservative, fragrance qs | |
| natural pH | 7 |
| Water qs | 100 g |

We claim:

1. Composition for washing keratinous materials, especially the hair and the skin, characterised in that it comprises, in an aqueous medium, at least one silicone, at least one surfactant possessing detergent properties and at least one alcohol having 27 to 44 carbon atoms and containing one or two ether and/or thioether or sulphoxide group(s), corresponding to the formula (I):

$$R_1-X+C_2H_3(OH)+CH_2-Y-R_2 \qquad (I)$$

in which $R_1$ and $R_2$, which may be identical or different, denote linear $C_{12}$ to $C_{20}$ alkyl groups;

X denotes an oxygen atom, a sulphur atom or a sulphoxide group;

Y denotes an oxygen atom, a sulphur atom, a sulphoxide group or a methylene group;

in the case where Y denotes a methylene group, the sum of the numbers of carbon atoms in $R_1$ and $R_2$ varies from 24 to 40, inclusive, and when Y does not denote a methylene group, the sum of carbon atoms in $R_1$ and $R_2$ varies from 24 to 40 inclusive; when X or Y denotes sulphoxide, Y or X does not denote sulphur.

2. Composition according to claim 1, characterised in that the alcohol having 27 to 44 carbon atoms corresponds to the formula (I) in which X denotes oxygen, Y denotes methylene and $R_1$ and $R_2$ denote radicals having 12 to 18 carbon atoms.

3. Composition according to claim 1, characterised in that the compound of formula (I) is a compound corresponding to the formula:

$$R_1-X_1+C_2H_3(OH)+CH_2-Y_1-R_2 \qquad (IV)$$

in which $R_1$ and $R_2$ have the same meaning as in claim 1;

$X_1$ denotes an oxygen atom of a sulphoxide group;

$Y_1$ denotes an oxygen atom or a methylene or sulphoxide group;

at least one of the symbols $X_1$ or $Y_1$ represents a sulphoxide group.

4. Composition according to claim 1, characterised in that the silicone is selected from polyorganosiloxanes which are insoluble in the composition and which take the form of oils, waxes, resins or gums.

5. Composition according to claim 1, characterised in that the polyorganosiloxanes are non-volatile polyorganosiloxanes selected from polyalkylsiloxanes, polyarylsiloxanes, polyalkylarylsiloxanes, silicone gums and resins and polyorganosiloxanes modified with organic functional groups, as well as mixtures thereof.

6. Composition according to claim 1, characterised in that (a) the polyalkylsiloxanes are selected from:

linear polydimethylsiloxanes containing terminal trimethylsilyl groups;
linear polydimethylsiloxanes containing terminal dimethylsilanol groups;
poly($C_1$-$C_{20}$ alkyl)siloxanes;
(b) the polyalkylarylsiloxanes are selected from:
linear and/or branched polydimethylmethylphenylsiloxanes and polydimethyldiphenylsiloxanes of viscosity between $1 \times 10^{-5}$ and $5 \times 10^{-2}$ m²/s at 25° C.;
(c) the silicone gums are selected from polydiorganosiloxanes having molecular masses of between 200,000 and 1,000,000, used alone or in the form of a mixture in a solvent;
(d) the resins consist of units:

$R_2SiO_{2/2}, RSiO_{3/2}, SiO_{4/2}$ in which units R represents a hydrocarbon group having from 1 to 6 carbon atoms or a phenyl group;
(e) the silicones modified with organic groups are selected from silicones containing in their structure one or more organic functional groups bound directly to the siloxane chain or bound via a hydrocarbon radical.

7. Composition according to claim 6, characterised in that the silicone gums used alone or in the form of a mixture are selected from the following structures:
polydimethylsiloxane/methylvinylsiloxane,
polydimethylsiloxane/diphenylsiloxane,
polydimethylsiloxane/phenylmethylsiloxane,
polydimethylsiloxane/diphenylsiloxane/methylvinylsiloxanes,
and the following mixtures:
mixtures formed from a polydimethylsiloxane (PDMS) hydroxylated at the end of the chain and a cyclic polydimethylsiloxane;
the mixtures formed from a polydimethylsiloxane gum and a cyclic silicone, and
mixtures of polydimethylsiloxanes of different viscosities.

8. Composition according to claim 6, characterised in that the silicones modified with organic groups are selected from polyorganosiloxanes containing
a) polyethylenoxy and/or polypropylenoxy groups;
b) substituted or unsubstituted amino groups;
c) thiol groups;
d) carboxylate groups;
e) alkoxy groups;
f) hydroxyalkyl groups corresponding to the following formula:

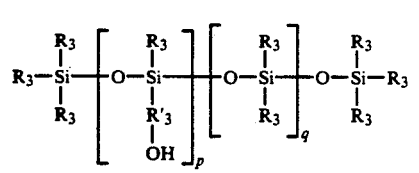

(V)

in which the radicals $R_3$, which may be identical or different, are selected from methyl and phenyl radicals, at least 60 mol % of the radicals $R_3$ denoting methyl; the radical $R'_3$ is a divalent $C_2$-$C_{18}$ carbon/hydrogen-based alkylene unit; p is between 1 and 30 inclusive; q is between 1 and 150 inclusive;
g) acyloxyalkyl groups corresponding to the following formula:

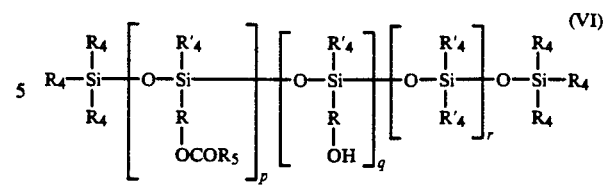

(VI)

in which:
$R_4$ denotes methyl, phenyl, —$OCOR_5$ or hydroxyl, it being possible for only one of the radicals $R_4$ per silicon atom to be OH;
$R'_4$ denotes methyl or phenyl; at least 60 mol % of all the radicals $R_4$ and $R'_4$ denoting methyl;
$R_5$ denotes $C_8$-$C_{20}$ alkyl or alkenyl;
R denotes a divalent, linear or branched $C_2$-$C_{18}$ carbon/hydrogen-based alkylene radical;
r is between 1 and 120 inclusive;
p is between 1 and 30;
q is equal to 0 or is less than 0.5 p, p+q being between 1 and 30; the polyorganosiloxanes of formula (VI) can contain groups

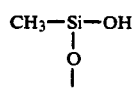

in proportions not exceeding 15% of the sum p+q+r;
h) alkylcarboxyl groups;
i) 2-hydroxyalkylsulphonate groups;
j) 2-hydroxyalkyl thiosulphate groups;
k) hydroxyacylamino groups.

9. Composition according to claim 1, characterised in that the polyorganosiloxanes are selected from linear polyalkylsiloxanes containing terminal trimethylsilyl groups, polyalkylarylsiloxanes, mixtures of two PDMS consisting of a gum and an oil of different viscosities, mixtures of organosiloxanes and cyclic silicones, and organopolysiloxane resins.

10. Composition according to claim 1, characterised in that the silicones are selected from volatile silicones.

11. Composition according to claim 10, characterised in that the volatile silicones are selected from:
cyclic silicones containing from 3 to 7 silicon atoms;
cyclic polymers of the dimethylsiloxane/methylalkylsiloxane type, of structure:

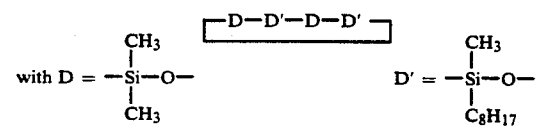

mixtures of cyclic silicones with organic compounds derived from silicon;
volatile linear silicones having 2 to 9 silicon atoms and of viscosity not exceeding $5 \times 10^{-6}$ m²/s at 25° C.

12. Composition according to any one of claims 1 to 11, characterised in that the detergent surfactants are selected from anionic, amphoteric, zwitterionic and nonionic surfactants or mixtures thereof.

13. Composition according to claim 12, characterised in that the anionic surfactants are selected from the alkali metal salts, magnesium salts, ammonium salts, amine salts or amino alcohol salts of the following compounds:

alkyl sulphates, alkyl ether sulphates, alkylamido ether sulphates, alkylaryl polyether sulphates, monoglyceride sulphates;
alkylsulphonates, alkylamide sulphonates, alkylarylsulphonates, olefin sulphonates, paraffin sulphonates;
alkylsulphosuccinates, alkyl ether sulphosuccinates, alkylamide sulphosuccinates;
alkylsulphosuccinamates;
alkylsulphoacetates;
alkyl phosphates, alkyl ether phosphates;
acylsarcosinates, acylisethionates, N-acyltaurinates; the alkyl or acyl radical of these various compounds consisting of a carbon chain containing from 12 to 20 carbon atoms;
the fatty acid salts with oleic, ricinoleic, palmitic and stearic acids;
the acids of coconut oil and of hydrogenated coconut oil;
the acyllactylates in which the acyl radical contains from 8 to 20 carbon atoms;
the polyoxyalkylenated carboxylic ether-acids corresponding to the formula:

$$R_6\text{---}(OC_3H_6)_p\text{---}(OC_2H_4)_n\text{---}OCH_2COOA \quad (VII)$$

in which $R_6$ denotes a linear or branched $C_8$-$C_{22}$ alkyl or alkenyl radical or a mixture of such radicals, a ($C_8$-$C_9$ alkyl)phenyl radical or $R_7$CONH—CH$_2$—CH$_2$— with $R_7$ denoting a linear or branched $C_{11}$-$C_{21}$ alkyl or alkenyl radical; n is an integer or decimal number between 2 and 24, p is an integer or decimal number between 0 and 6; A denotes a hydrogen atom or alternatively Na, K, Li, ½ Mg or a monoethanolamine, ammonium or triethanolamine residue.

14. Composition according to claim 12, characterised in that the nonionic surfactants are selected from:
polyethoxylated, polyoxypropylenated or polyglycerolated alcohols, alkylphenols and fatty acids having a fatty chain containing 8 to 18 carbon atoms, the number of ethylene oxide or propylene oxide groups being between 2 and 50 and the number of glycerol groups being between 2 and 30; copolymers of ethylene and propylene oxides, condensates of ethylene and propylene oxides with fatty alcohols; polyethoxylated fatty amides; polyethoxylated fatty amines; fatty acid ethanolamides; fatty acid esters of sorbitan, oxyethylenated or otherwise; fatty acid esters of polyethylene glycol; phosphoric triesters; fatty acid esters of sucrose; alkylpolyglycosides; and oxides of fatty amines.

15. Composition according to claim 12, characterised in that the nonionic surfactant is selected from the compounds of formula:

$$R_8O\text{---}(CH_2\text{---}CH\text{---}O)_{\overline{m}}H \quad (VIII)$$
$$\quad\quad\quad\quad\quad | $$
$$\quad\quad\quad\quad CH_2OH$$

in which $R_8$ denotes an alkyl radical containing 10 to 14 carbon atoms or a mixture of such radicals and m is an integral or decimal statistical value from 2 to 10;
the compounds of formula:

$$R_9\text{---}CONH\text{---}CH_2\text{---}CH_2\text{---}O\text{---}CH_2\text{---}CH_2\text{---}O(CH_2\text{---}CHOH\text{---}CH_2\text{---}O)_{\overline{n}}H \quad (IX)$$

in which $R_9$ denotes an alkyl and/or alkenyl radical having from 11 to 17 carbon atoms or a mixture of such radicals and n denotes an integral or decimal statistical value from 1 to 5,
the compounds of formula:

$$R_{10}\text{---}CHOH\text{---}CH_2\text{---}O\text{---}(CH_2\text{---}CHOH\text{---}CH_2\text{---}O)_{\overline{p}}H \quad (X)$$

in which $R_{10}$ denotes an aliphatic, cycloaliphatic or arylaliphatic radical preferably having 7 to 21 carbon atoms and mixtures thereof, the aliphatic chains denoting, in particular, alkyl chains which can contain from 1 to 6 ether, thioether and/or hydroxymethylene groups and p is between 2 and 10;
the compounds prepared by acid-catalysed condensation of between 2 and 10, moles of glycidol per mole of alcohol or of alpha-diol containing 10 to 14 carbon atoms;
poly(hydroxypropyl ether) compounds prepared by polyaddition of glycerol monochlorohydrin to a polyhydroxylated organic compound in the presence of a strong base.

16. Composition according to claim 12, characterised in that the amphoteric or zwitterionic surfactants are selected from derivatives of secondary or tertiary aliphatic amines in which the aliphatic radical is a linear or branched chain containing from 8 to 18 carbon atoms and which contains at least one anionic carboxyl, sulphonate, sulphate, phosphate or phosphonate group conferring solubility in water;
alkylbetaines, sulphobetaines, amidobetaines or amidosulphobetaines.

17. Composition according to claim 1, characterised in that mixtures of surfactants, selected from mixtures of anionic surfactants and amphoteric, zwitterionic or nonionic surfactants, are used.

18. Composition according to claim 1, characterised in that the silicones are used in the compositions according to the invention in proportions of between 0.05 and 20%, by weight relative to the total weight of the composition.

19. Composition according to claim 1, characterised in that the alcohols containing ether and/or thioether or sulphoxide groups of formula (I) or (IV) are used in sufficient proportions to provide for the homogeneity, thickening and opalescence of the compositions.

20. Composition according to claim 19, characterised in that the alcohols containing ether and/or thioether or sulphoxide groups of formula (I) or (IV) are present in proportions of between 0.1 and 10% by weight relative to the total weight of the composition.

21. Composition according to claim 1, characterised in that the surfactants are present in a sufficient proportion to impart a detergent character to the composition.

22. Composition according to claim 21, characterised in that the surfactants are present in proportions of between 5 and 50% by weight relative to the total weight of the composition.

23. Composition according to claim 1, characterised in that the pH is between 3 and 9.

24. Composition according to claim 1, characterised in that the aqueous medium consists of water or of a mixture of water and a cosmetically acceptable solvent selected from lower alcohols, alkylene glycols and glycol ethers.

25. Composition according to claim 1, characterised in that the composition contains, in addition, viscosity regulators selected from electrolytes, hydrotropes or thickening agents, present in proportions which can range up to 10% by weight relative to the total weight of the composition.

26. Composition according to claim, characterised in that it contains, in addition, up to 3% of pearlescence and/or opacifying agents.

27. Composition according to claim 7, characterised in that it contains, in addition, one or more adjuvants intended for improving the cosmetic properties, selected from cationic surfactants, anionic or nonionic or cationic or amphoteric polymers or optionally quaternised proteins.

28. Composition according to claim 27, characterised in that the cationic polymers are selected from polymers containing primary, secondary, tertiary and/or quaternary amino groups forming part of the polymer chain or directly linked to the latter and having a molecular weight of approximately 500 to approximately 5,000,000.

29. Composition according to claim 28, characterised in that the cationic polymers are selected from cationic polysaccharides and quaternary polyammonium compounds.

30. Composition according to claim 27, characterised in that the amphoteric polymer is a copolymer of dialyldialkylammonium and acrylic or methacrylic acid and/or a polymer derived from chitosan.

31. Composition according to claim 1, characterised in that it contains various cosmetically acceptable adjuvants selected from fragrances, preservatives, sequestering agents, foam synergists, foam stabilisers and acidifying or alkalinising agents.

32. A shampoo comprising the composition as defined in claim 1.

33. A shower gel comprising the composition as defined in claim 1.

34. Process for washing and conditioning keratinous material, characterised in that at least one composition as defined in claim 1 is applied to the material, and in that, after an exposure time, the treated material is rinsed with water.

* * * * *